United States Patent [19]
Bruzzese et al.

[11] 3,937,815
[45] Feb. 10, 1976

[54] LYSOZYME DERIVATIVES
[75] Inventors: Tiberio Bruzzese; Rodolfo Ferrari, both of Milan, Italy
[73] Assignee: SPA—Societa Prodotti Antibiotici S.p.A., Italy
[22] Filed: Dec. 5, 1975
[21] Appl. No.: 530,022

[52] U.S. Cl............... 424/94; 260/112.5 R; 195/63; 424/177
[51] Int. Cl.$^2$................. C07C 103/52; A61K 37/00
[58] Field of Search .......... 260/112.5; 424/177, 94; 195/63

[56] References Cited
UNITED STATES PATENTS

| 3,242,056 | 3/1966 | Prevost | 424/94 |
| 3,282,782 | 11/1966 | Scolari | 424/94 |
| 3,859,435 | 1/1975 | Bruzzese et al. | 424/94 |

OTHER PUBLICATIONS

Ryan: Arch. Biochem. Biophys., 126, 407–17 (1968).
Faure et al.: Chem. Abstr. 70:93335w(1969).
Cherkasov et al.: Chem. Abstr. 67:70735a(1967).
Felsenfeld et al.: Chem. Abstr. 66:82643m(1967).

*Primary Examiner*—Lewis Gotts
*Assistant Examiner*—Reginald J. Suyat
*Attorney, Agent, or Firm*—Wenderoth, Lind & Ponack

[57] ABSTRACT

The present invention provides new salts and complexes of lysozyme and of basic derivatives of lysozyme with bile acids, processes for the preparation thereof and the pharmaceutical use thereof.

10 Claims, No Drawings

LYSOZYME DERIVATIVES

BACKGROUND OF THE INVENTION

As is known, lysozyme is a natural protein found in biological fluids which has an enzymatic activity and a marked lytic action on various saprophytic and pathogenic bacteria. From a biological point of view, it has a defensive role, i.e. it can protect the organism from attack by pathogenic viral and bacterial mecroorganisms and, as such, lysozyme is considered to be an endogenous antibiotic.

The structure of lysozyme has been completely elucidated; it consists of 129 amino acid residues, the radicals of dibasic amino acids being particularly abundant, there being 11 residues of arginine, six residues of lysine and one of histidine. This particular composition of lysozyme gives it a strong positive charge and a high isoelectric point (around 11), which differentiates it from the majority of the other proteins, in which the acidic character generally prevails.

In view of the biological interest connected with the basic properties of lysozyme, numerous derivatives of lysozyme have also been prepared, these having an even higher positive charge than lysozyme itself. Some of these derivatives (see British Patent Specification No. 1,209,214) are obtained, for example, by blocking the acid functions of the dicarboxylic amino acid residues (aspartic acid and glutamic acid) by esterification or by converting the $\epsilon$-amino-groups of the lysine radicals into the more basic $\epsilon$-guanidino-groups to give radicals of homoarginine or by using both procedures.

Biologically, all the above derivatives retain or enhance the antiviral activity of the original lysozyme on the RNA- and the DNA-viruses and are able to form complexes with them by neutralisation of the opposite charges, with consequent precipitation. The guanidyl-lysozymes also retain the typical anti-bacterial lytic activity of lysozyme.

The above-described properties enable lysozyme and its more basic derivatives to form water-soluble salts with strong acids, for example hydrochloric acid, as well as with weak acids, for example ascorbic acid. Lysozyme and its basic derivatives also have a marked tendency to form complexes, which are generally insoluble, with many anionic macromolecules, for example with nucleic acids and with electronegative colloids.

SUMMARY OF THE INVENTION

According to the present invention, there are provided salts and complexes of lysozyme and of basic derivatives of lysozyme with bile acids, which salts and complexes are water-soluble or only slightly water-soluble.

In other words, these anionic surfactants (bile acids) are also able to bind with the basic nitrogen atoms of the protein molecule (lysozyme) to produce ionic bonds. Other forces can also be involved in the interactions between the bile acids and the protein and thus the surfactant may be associated, in the form of a complex, with the protein in excess of the stoichiometric amounts predicted by the number of cationic charges.

DETAILED DESCRIPTION OF THE INVENTION

These new substances are of great potential interest from a pharmacological point of view because they appear to enhance the basic antiviral activity of the lysozyme compounds by a mechanism of action which can be correlated to the surfactant action of the bile acids or also by synergism with a specific antiviral activity of the bile acids themselves.

It is already known that, when surface-active agents are incubated with microorganisms, they apparently react with the cell membrane; cell constituents, such as potassium, amino acids, purines and pyrimidines, diffuse into the incubation medium and protoplasts are rapidly lysed. Thus, the increased permeability of the biological membranes, caused by the surfactants, synergistically potentiates the known antiviral and antibacterial activities of lysozyme and of its basic derivatives.

Typical fields of action of the new substances according to the present invention include the therapeutic treatment of herpes simplex and herpes zoster, recurrent aphthosis, rhinitis and colitis of viral origin and other viral diseases, including certain carcinogenic diseases.

The particular affinity towards the biliary routes makes the new compounds potentially more specifically active in this direction. The antiviral activity of lysozyme is accompanied by its anti-inflammatory and anti-toxic actions, which are useful for combating a large variety of pathological affections.

The preparation of the new salts and complexes is quite simple. Generally, lysozyme or a basic derivative thereof is reacted directly, in the form of the free base, with a slight excess of a bile acid. The reaction is usually carried out in an aqueous medium or in a medium containing organic solvents, preferably at ambient temperature but in any case at a temperature which is sufficiently low as to not cause any denaturating of the protein substance. The reaction time is relatively short and is generally less than 4 – 6 hours. As the salification proceeds, the lysozyme and the bile acid, which are completely or partly insoluble in water, gradually pass into solution, giving pH values around neutrality. After filtering off possible traces of excess and, therefore, insoluble matter, the desired salt is isolated by lyophilisation, concentration to dryness at a reduced temperature and pressure or by precipitation with organic solvents. In other cases in which the salt formed is only sparingly soluble in water, it can be isolated directly by filtration. Instead of a direct interaction between the basic protein and the bile acid, the preparation can, in some cases, be carried out more advantageously by reacting a simple salt of the lysozyme compound, for example lysozyme hydrochloride, with a salt of a bile acid, for example a sodium salt. A double decomposition reaction rapidly takes place to give the desired compound; the means and the conditions of the reaction are similar to those already described above.

Since different types of basic groups are present in lysozyme and in its derivatives, some of which have different degrees of basicity, it is also possible to obtain compounds with different degrees of salification or complexing, i.e., complete or partial, and the content of the individual components can, therefore, vary widely. It is also possible to obtain double salts containing different acidic anions. In all the cases, the compounds obtained can be purified, if necessary, for example by washing with appropriate organic solvents which can dissolve and eliminate any unreacted bile acid present.

Examples of basic derivatives of lysozyme which can be used for the preparation of the new salts include lysozyme methyl ester, guanidyl-lysozyme, guanidyl-lysozyme methyl ester and alkylamidino-lysozymes.

The bile acids which can be used include, for example, cholic acid, desoxycholic acid, dehydrocholic acid, glycocholic acid, taurocholic acid and the like.

The new compounds are colourless, crystalline solids, without a definite melting point. They possess varying degrees of solubility in water and all of them are insoluble in common organic solvents, for example diethyl ether, petroleum ether, ligroin, benzene and cyclohexane. They are generally split by acids and by strong alkalis.

The analysis of the new compounds can be carried out by direct titration of the components. The lysozyme content in the new compounds can be determined by measuring the lysis of *Micrococcus lysodeikticus* suspensions (see A. U. Di Nardo, Igiene Moderna, 60, 485/1967) and by evaluating the absorption of the ultra-violet light at 281 m$\mu$ in accordance with the methods described in the literature. The content of bile acid is usually determined, after acidification with hydrochloric acid, by extraction with chloroform or by direct filtration of the acid released and subsequent titration with aqueous sodium hydroxide solution, using phenolphthalein as indicator.

In some cases, it is more convenient to use the characteristic colorimetric reactions; for example, dehydrocholic acid can also be determined by the colour reaction with m-dinitrobenzene in an alkaline medium by G. Saba's method (see J. Biochem., 30, 61/1939) as modified by C. Bergamini and W. Versorese (see Lo Sperimentale, 4, 79/1953); taurocholic acid can also be assayed colorimetrically after direct reaction with 65% sulphuric acid by the method described in the literature (see T. Inutsuka, Fukuoka Igaku-Zassi, 48, 733/1957).

The following Examples are given for the purpose of illustrating the present invention:

EXAMPLE 1

9.4 g. desoxycholic acid were suspended in 150 ml. distilled water, whereafter a stoichiometric quantity of 1 N aqueous sodium hydroxide solution was cautiously added. The solution thus obtained was decolorised with charcoal and filtered. A solution of 20 g. lysozyme hydrochloride in 150 ml. distilled water was then added, while stirring. An abundant precipitate formed immediately. The reaction mixture was stirred for another 30 minutes and the product was separated by centrifuging, washed by slurrying with 50 ml. water and isolated by the same procedure. After drying under vacuum at ambient temperature and subsequent purification by washing with diethyl ether, 24.5 g. lysozyme desoxycholate were obtained in the form of a colourless, crystalline solid, which was sparingly soluble in water. The analysis gave a lysozyme content of 78% and a desoxycholic acid content of about 18% (water content 4%).

EXAMPLE 2

In a manner analogous to that described in Example 1 but reacting the sodium salt of desoxycholic acid with guanidyl-lysozyme hydrochloride, there was obtained the desoxycholate of guanidyl-lysozyme, having the same physical properties and a similar analytical composition with regard to the content of bile acid and lysozyme derivative.

EXAMPLE 3

The reaction of sodium desoxycholate with lysozyme methyl ester hydrochloride in a manner analogous to that described in Example 1, gave the corresponding desoxycholate of methyl-lysozyme.

EXAMPLE 4

By reacting sodium desoxycholate with guanidyl-lysozyme methyl ester hydrochloride in a manner analogous to that described in Example 1, there was obtained the desoxycholate of methyl guanidyl-lysozyme.

EXAMPLE 5

10 g. lysozyme (free base) were suspended in 100 ml. distilled water and mixed with 3.5 g. desoxycholic acid. The suspension was stirred at ambient temperature for 2 hours. The reaction mixture was then evaporated to dryness at a reduced temperature and pressure and the residue obtained was washed thoroughly with chloroform, by slurrying, to eliminate excess free desoxycholic acid. After drying under vacuum, the desoxycholate of lysozyme was obtained. It had the same physico-chemical and analytical characteristics as the product of Example 1.

EXAMPLE 6

In a manner analogous to that described in Example 5 but reacting desoxycholic acid with guanidyl-lysozyme, there was obtained the desoxycholate of guanidyl-lysozyme in the form of a colourless, crystalline substance, which corresponded analytically to the compound obtained in Example 2.

EXAMPLE 7

15 g. lysozyme (free base) were suspended in 100 ml. distilled water and then 3 g. dehydrocholic acid were added portionwise to give a solution. Traces of excess dehydrocholic acid were removed by filtration, whereafter the filtrate was decolorised with charcoal and lyophilised. The residue consisted of the dehydrocholate of lysozyme in substantially quantitative yield; the compound was a colourless, crystalline solid which was very soluble in water. The analysis gave a content of lysozyme of 81% and a content of dehydrocholic acid of about 16%.

EXAMPLE 8

Dehydrocholic acid was reacted with guanidyl-lysozyme in a manner analogous to that described in Example 7 to give the dehydrocholate of guanidyl-lysozyme which had the same physical properties and a similar analytical composition with regard to the content of bile acid and of guanidyl-lysozyme, as the product of Example 7.

EXAMPLE 9

20 g. lysozyme hydrochloride in 50 ml. distilled water were added, while stirring, to a solution of 9.6 g. dehydrocholic acid suspended in 20 ml. distilled water and mixed with a stoichiometric quantity of 1 N aqueous sodium hydroxide solution. The reaction mixture was kept for 3 hours, while stirring, at 0°C. The crystals formed were filtered off and dried in a vacuum to give a crude product (21.5 g.) which was washed twice by slurrying with a total of 300 ml. chloroform to remove free dehydrocholic acid and then filtered and dried again in a vacuum. 19 g. of the dehydrocholate of lysozyme were obtained in the form of an almost colourless crystalline solid. The analytical composition was similar to that of the product of Example 7, the lysozyme content being 80% and the dehydrocholic acid content being 17%.

EXAMPLE 10

The reaction of sodium dehydrocholate with guanidyl-lysozyme hydrochloride in a manner analogous to that described in Example 9 gave the corresponding dehydrocholate of guanidyl-lysozyme.

EXAMPLE 11

A solution of 15 g. lysozyme hydrochloride in 100 ml. distilled water was added, while stirring, to a solution obtained by dissolving 10.3 g. sodium taurocholate in 150 ml. distilled water and then decolorising with charcoal. The suspension obtained was kept for 30 minutes, while stirring, at ambient temperature and then the product was removed by filtration, washed with 50 ml. water, filtered and dried in a vacuum. The taurocholate of lysozyme thus obtained in a yield of 20 g., was a crystalline, almost colourless solid. The analysis gave a content of lysozyme of 74% and a content of taurocholic acid of 21% (water content = 4%).

The present invention also includes within its scope pharmaceutical compositions containing the new salts and complexes of lysozyme and of basic derivatives of lysozyme. These pharmaceutical compositions can be administered orally, rectally or parenterally in admixture with a solid or liquid pharmaceutical carrier.

Solid compositions for oral administration include compressed tablets, pills, dispersible powders and granules. In such solid compositions, one of the new salts or complexes is admixed with at least one inert diluent, such as calcium carbonate, starch, alginic acid or lactose. Solid compositions for rectal administration can be made by mixing the active materials with conventional suppository bases. The solid compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents and sweetening and flavouring agents.

The compositions according to the present invention, for oral administration, include capsules of absorbable material, such as gelatine, containing one of the new salts or complexes, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The percentage of the new salt or complex in the compositions of the present invention may be varied, it being necessary that it should constitute a proportion such that a suitable dosage for the desired therapeutic effect shall be obtained. In general, the preparations of the present invention should be administered orally, rectally or parenterally to give 25 to 100 mg. of active substance per day. Parenteral administration can be, for example, by the intramuscular, intravenous or intrabursal routes.

The following Examples illustrate pharmaceutical compositions according to the present invention:

EXAMPLE 12

| 500 mg. tablets are prepared containing: | |
|---|---|
| lysozyme desoxycholate | 250 mg. |
| starch | 150 mg. |
| lactose | 95 mg. |
| magnesium stearate | 5 mg. |

EXAMPLE 13

| 500 mg. tablets are prepared containing: | |
|---|---|
| lysozyme taurocholate | 300 mg. |
| starch | 180 mg. |
| magnesium stearate | 20 mg. |

The compositions described in the two above Examples 12 and 13 are intended for oral administration to humans for the alleviation and treatment of viral infections.

We claim:

1. A salt or complex of a member selected from the group consisting of lysozyme, guanidyl lysozyme, methyl lysozyme and methyl guanidyl lysozyme with a bile acid.

2. A salt or complex according to claim 1 which is lysozyme desoxycholate.

3. A salt or complex according to claim 1 which is guanidyl-lysozyme desoxycholate.

4. A salt or complex according to claim 1 which is methyl lysozyme desoxycholate.

5. A salt or complex according to claim 1 which is methyl guanidyl-lysozyme desoxycholate.

6. A salt or complex according to claim 1 which is lysozyme dehydrocholate.

7. A salt or complex according to claim 1 which is guanidyl-lysozyme dehydrocholate.

8. A salt or complex according to claim 1 which is lysozyme taurocholate.

9. A salt or complex according to claim 1 wherein the bile acid is selected from the group consisting of cholic acid, desoxycholic acid, dehydrocholic acid, glycocholic acid, taurocholic acid.

10. A pharmaceutical composition comprising a salt or complex of a member selected from the group consisting of lysozyme, guanidyl lysozyme, methyl lysozyme and methyl guanidyl lysozyme with a bile acid, in admixture with a solid or liquid pharmaceutical diluent or carrier.

* * * * *